US008882924B2

(12) United States Patent
O'Connor

(10) Patent No.: US 8,882,924 B2
(45) Date of Patent: Nov. 11, 2014

(54) PRETREATMENT OF SOLID BIOMASS MATERIAL COMPRISING CELLULOSE WITH IONIC LIQUID MEDIUM

(75) Inventor: Paul O'Connor, Hoevelaken (NL)

(73) Assignee: KiOR, Inc., Pasadena, TX (US)

(*) Notice: Subject to any disclaimer, the term of this patent is extended or adjusted under 35 U.S.C. 154(b) by 330 days.

(21) Appl. No.: 13/391,760

(22) PCT Filed: Sep. 1, 2010

(86) PCT No.: PCT/IB2010/002389
§ 371 (c)(1),
(2), (4) Date: Mar. 27, 2012

(87) PCT Pub. No.: WO2011/027223
PCT Pub. Date: Mar. 10, 2011

(65) Prior Publication Data
US 2012/0178921 A1    Jul. 12, 2012

Related U.S. Application Data

(60) Provisional application No. 61/238,730, filed on Sep. 1, 2009.

(51) Int. Cl.
C08H 8/00       (2010.01)
C12P 19/14      (2006.01)
C12P 19/02      (2006.01)
C10B 53/02      (2006.01)
C10B 57/08      (2006.01)
C10G 3/00       (2006.01)
C13K 1/02       (2006.01)

(52) U.S. Cl.
CPC . C08H 8/00 (2013.01); C12P 19/14 (2013.01); C12P 19/02 (2013.01); C10B 53/02 (2013.01); C10B 57/08 (2013.01); C10G 3/00 (2013.01); C13K 1/02 (2013.01); Y02E 50/18 (2013.01); C12P 2201/00 (2013.01); Y02E 50/14 (2013.01); Y02E 50/16 (2013.01); C10G 2300/1014 (2013.01)
USPC ................ 127/34; 127/37; 536/128; 435/105

(58) Field of Classification Search
USPC ..................... 127/34, 37; 536/128; 435/105
See application file for complete search history.

(56) References Cited

U.S. PATENT DOCUMENTS

| | | | |
|---|---|---|---|
| 5,410,034 A | 4/1995 | Isogai | |
| 6,824,559 B2 * | 11/2004 | Michal | 623/1.15 |
| 6,824,599 B2 | 11/2004 | Swatloski et al. | |
| 7,503,981 B2 | 3/2009 | Wyman et al. | |
| 2007/0161095 A1 | 7/2007 | Gurin | |
| 2008/0185112 A1 * | 8/2008 | Argyropoulos | 162/9 |
| 2008/0190013 A1 | 8/2008 | Argyropoulos | |
| 2008/0227162 A1 | 9/2008 | Varanasi | |
| 2008/0227972 A1 | 9/2008 | Yamaguchi | |
| 2009/0011473 A1 | 1/2009 | Varanasi | |
| 2010/0163018 A1 | 7/2010 | Gifford | |

FOREIGN PATENT DOCUMENTS

| | | |
|---|---|---|
| DE | 102004031025 | 12/2005 |
| EP | 2006354 | 12/2008 |
| EP | 2033974 | 3/2009 |
| GB | 2451046 | 1/2009 |
| WO | WO/03029329 | 4/2003 |
| WO | WO/2005017252 | 2/2005 |
| WO | WO/2006119357 | 11/2006 |
| WO | WO/2007112090 | 10/2007 |
| WO | WO/2008043837 | 4/2008 |
| WO | WO/2008098036 | 8/2008 |
| WO | WO/2008112291 | 9/2008 |
| WO | WO/2008119770 | 10/2008 |
| WO | WO/2010100126 | 9/2010 |
| WO | WO/2011027220 | 3/2011 |
| WO | WO/2011028776 | 3/2011 |
| WO | WO/2011028783 | 3/2011 |
| WO | WO/2011028788 | 3/2011 |

OTHER PUBLICATIONS

Bridgwater A.V. "Catalysis in thermal biomass conversion" Applied Catalysis, A: general, Elsevier Science, Amsterdam,, NL, 1994, 116, 5-47.
Cuissinat et al. "Swelling and dissolution of cellulose. Part IV: Free floating cotton and wood fibres in ionic liquids." Carbohydrate Polymers, Applied Science Publishers, Ltd. Barking, GB, 2008, 72, 590-596.
Duchemin B.J. e al. "All-cellulose composites by partial dissolution in the ionic liquid 1-butyl-3-methylimidazolium chloride" Composites Part A: Applied Science and manufacturing, Elsevier Science Publishers, Amsterdam, NL, 2009, 40, 2031-2037.
Fischer S. et al. "The behaviour of cellulose in hydrated melts of the composition LiX.nH2O (X=I-, NO3-, CH3C00-, ClO4)" Cellulose, Kluwer Academic Publishers, 1999, 6, 213-219.
Fischer S. et al. "Evaluation of molten inorganic salt hydrates as reaction medium for the derivatization of cellulose" Cellulose, Kluwer Academic Publishers, 2002, 9, 293-300.
Fischer S. et al. "Inorganic molten slats as solvents for cellulose" Cellulose, 2003, 227-236.
Fort et al. "Can ionic liquids dissolve wood? Processing and analysis of lignocellulosic materials with 1-n-butyl-3-methylimidazolium chloride", Green Chemistry, Royal Society of Chemistry, Cambridge, GB, 2007, 9, 63-69.

(Continued)

Primary Examiner — David M Brunsman
(74) Attorney, Agent, or Firm — Greenberg Traurig, LLP; Natalie Salem

(57) ABSTRACT

A process for pretreating a solid, cellulose-containing biomass material which pretreatment comprises contacting the solid biomass material with an Ionic Liquid medium under sub-solvating conditions. The pretreatment results in an opening up of the texture of the solid biomass material, while no or a limited amount of biomass material is dissolved. The Ionic Liquid medium preferably is an inorganic molten salt hydrate. The pretreated biomass material can be as a feedstock in any process that benefits from the change in texture resulting from the pretreatment.

19 Claims, No Drawings

(56) References Cited

OTHER PUBLICATIONS

Heinze T. et al. "Unconventional methods in cellulose functionalization" Progress in Polymer Science, Pergamon Press, Oxford, GB, 2001, 26, 1689-1762.

Kilpelainen I et al. "Dissolution of wood in ionic liquids" J. Agric. Food Chem. 2007, 55, 9142-9148.

Li C. et al. "Comparison of dilute acid and ionic liquid pretreatment of switchgrass: Biomass recalcitrance, delignification and enzymatic saccharification", Bioresource Technology Elsevier BV GB 2010 101 4900-4906.

Salanti A. et al. "Characterization of waterlogged wood by MMR and GPC techniques", Microchemical Journal, 2010, 95, 345-352.

Schall C. et al. "Ionic liquid pretreatment of lignocellulosic for biofuels production", American Chemical Society, Abstract of paper at the National Meeting, American Chemical Society, US, 2008, 236.

Sheldrake G.N. et al. "Dicationic molten salts (ionic liquids) as re-usable media for the controlled pyrolysis of cellulose to anhydrosugars", Green Chemistry, Royal Society of Chemistry, Cambridge, GB, 2007, 9, 1044-1046.

Singh, S. et al. "Visualization of biomass solubilization and cellulose regeneration during ionic liquid pretreatment of switchgrass" Biotechnology and Bioengineering, 2009, 104, 68-75.

Takashi Hosoya et al. "Influence of inorganic matter on wood pyrolysis at gasification temperature", Journal of Wood Science: Official Journal of the Japan Wood Research Society, Springer Verlag, TO, 2007, 53, 351-357.

International Search Report in International Application No. PCT/IB2010/002389 mailed Feb. 2, 2011.

Fischer S. "Unconventional Dissolution and Derivatization of Cellulose" Lezinger Berichte, 2004, 83:71-78.

* cited by examiner

PRETREATMENT OF SOLID BIOMASS MATERIAL COMPRISING CELLULOSE WITH IONIC LIQUID MEDIUM

RELATED APPLICATIONS

This application is a National Phase application of International Application No. PCT/IB2010/002389 filed Sep. 1, 2010, which claims benefit of and priority to U.S. provisional patent application Ser. No. 61/238,730, filed Sep. 1, 2009, the content of each of the foregoing applications is incorporated herein by reference in its entirety.

BACKGROUND OF THE INVENTION

1. Field of the Invention

The invention relates generally to a process for pretreating cellulose-containing biomass materials, in particular lignocellulosic biomass materials.

2. Description of the Related Art

There is an interest in converting biomass materials to liquid fuels. In particular lignocellulosic biomass materials are attractive starting materials, as they are abundantly available and have no alternate use as food materials.

Gasification of biomass to syngas, followed by a Fischer-Tropsch process for converting syngas to liquid hydrocarbons, is one process being proposed for the conversion of biomass materials to liquid fuels. This approach is inherently inefficient, as gasification breaks down the biomass material to very small molecules, which then need to be built back up to larger ones. Moreover, gasification involves oxidation, which is directionally away from the formation of hydrocarbons.

Pyrolysis, in particular flash pyrolysis, is being studied as an alternate route to hydrocarbons from biomass. It has been found that short reaction times favor the formation of liquid reaction products, at the expense of gaseous reaction products.

Pyrolysis processes are hampered by the inherent stability of lignocellulose, which can be viewed as a composite of lignin, cellulose, and hemicellulose. Relatively severe reaction conditions are necessary in pyrolysis processes in order to open up the texture of the lignocellulose composites. Yet, these severe reaction conditions cause over-cracking of the primary pyrolysis products, resulting in high coke and gas yields.

Thus, there is a need for a pretreatment process in which the texture of the lignocellulose composite is opened-up, so that it can be converted in a subsequent process, such as a pyrolysis, under less severe conditions than those required for biomass material that has not been pretreated.

It has been known to dissolve cellulose in Ionic Liquids. S. Fischer et al., "*Inorganic molten salts as solvents for cellulose*", Cellulose 10: 227-236, 2003, discloses the use of various molten salt systems as solvent media for cellulose. The aim is complete dissolution of the cellulose.

Sheldrake and Schleck, "*Dicationic molten salts (ionic liquids) as re-usable media for the controlled pyrolysis of cellulose to anhydrosugars*", Green Chem. 2007, pp 1044-1046, reports on low temperature pyrolysis of cellulose in ionic liquid media. The starting material is pure cellulose. Pyrolysis is carried out with the cellulose in solution.

Thus, there is a need for a pretreatment process for cellulose-containing biomass materials, in particular lignocellulosic biomass materials.

BRIEF SUMMARY OF THE INVENTION

The present invention addresses these problems by providing a process for pretreating a solid, cellulose-containing biomass material, said process comprising the step (i) of contacting the solid biomass material with an Ionic Liquid medium under sub-solvating conditions.

DETAILED DESCRIPTION OF THE INVENTION

Prior art processes involving contacting cellulose with an Ionic Liquid medium are aimed at as full a dissolution of cellulose in the Ionic Liquid medium as possible. This is accomplished, in general, by a proper selection of the Ionic Liquid medium. For example, dicationic organic Ionic Liquids are, as a rule, better solvents for cellulose than are monocationc organic Ionic Liquids. Halogen anions, in particular chloride ions, are believed to be favorable for cellulose dissolution. Of the inorganic cations, rankings have been published of their respective cellulose dissolution properties.

The solvent properties of many Ionic Liquids vary considerably with the amount of water present in the Ionic Liquid medium. Many organic Ionic Liquids lose their dissolving powers in the presence of even small amounts of water, for which reason it has been suggested to operate under a dry gas atmosphere, commonly nitrogen or argon, to prevent water uptake from ambient air.

Inorganic molten salt hydrates, on the other hand, require the presence of water. Zinc chloride hydrate, $ZnCl_2 \cdot xH_2O$, for example, is a solvent for cellulose when x is in the range of from about 0.5 to about 6. Maximum dissolution properties are reached when x=4.

Another parameter affecting the cellulose dissolution properties of Ionic Liquids is temperature. As a general rule, for a specific Ionic Liquid, an increase in temperature results in a more rapid and more complete dissolution of cellulose. For organic Ionic Liquids the upper limit of temperature is generally determined by the thermal stability of the organic cation. For inorganic molten salts the upper limit is generally near 100° C., when too much water is lost from the molten salt hydrate due to evaporation. Higher temperatures are achievable when pressurized vessels are used.

Dissolution of cellulose is further enhanced by causing hydrolysis of dissolved cellulose to glucose (or xylose, in the case of hemicellulose). Hydrolysis of cellulose is catalyzed by Brønstedt acids, in particular mineral acids.

By contrast, the aim of the pretreatment process of the present invention is to avoid or minimize dissolution of cellulose and hemicellulose from the cellulose-containing biomass material. Thus, the present invention relates to a process for pretreating a solid, cellulose-containing biomass material, said process comprising the step (i) of contacting the solid biomass material with an Ionic Liquid medium under sub-solvating conditions.

The biomass material can be any cellulose-containing biomass material. For example, the biomass material can comprise aquatic biomass material, such as algae. Aquatic biomass material offers several advantages. Aquatic plants are more efficient than are land plants in converting solar energy into biomass material. In addition, many types of aquatic plants do not require a supply of fresh water, and in fact thrive in sea water or brackish water. On the other hand, aquatic biomass generally contains large amounts of water, which can be hard to remove. In particular micro-algae are difficult to separate from much of the water occluded in the plant cells. Many forms of Ionic Liquid media have a low tolerance for moisture.

Another drawback of aquatic biomass is the relatively high mineral content. Minerals interfere with the solvent properties of Ionic Liquid media in ways that are poorly understood, if understood at all.

Land-based plants generally contain cellulose in the form of lignocellulose, which is a natural composite of lignin and cellulose, generally further comprising hemicellulose. Some known Ionic Liquid media are capable of dissolving both cellulose and lignin. These media are naturally capable of dissolving the lignocellulose composite. Dissolved lignin can interfere with the further processing of dissolved cellulose. It is therefore often desirable to remove dissolved lignin from the Ionic Liquid medium, or to prevent lignin from becoming dissolved.

Many lignocellulosic biomass materials for example bagasse, contain large amounts of minerals. Other lignocellulosic materials, such as the sap wood part of a tree, contain relatively small amounts of minerals. In general, however, tree-based biomass feedstock comprises bark and leaves, which are both mineral-rich.

It is in general not possible to contact biomass material with an Ionic Liquid medium without introducing minerals in quantities large enough to interfere with the solvent properties of the Ionic Liquid medium.

In a preferred embodiment, the process of the present invention comprises subjecting the biomass material to a demineralization step. This demineralization step preferably is carried out before contacting the biomass material with the Ionic Liquid medium. In the demineralization step at least part of the minerals are removed from the biomass material.

The demineralization step can comprise contacting the biomass material with a solvent for the minerals, that is, a material, usually a liquid, in which the minerals present in the biomass material readily dissolve. The demineralization step further comprises separating the solvent (in which at least part of the minerals are dissolved) from the biomass material.

It is advantageous to contact the biomass material with the solvent in the form of small particles, having a median particle size in the range of from 100 µm to 10 cm, preferably from 1000 µm to 3 cm. It is further advantageous to apply mechanical action while contacting the biomass material with the solvent. Examples of mechanical action include kneading, high shear mixing, wet milling, and the like.

In general the demineralization step is carried out at a temperature in the range of from 25° C. to 200° C.

In one embodiment the biomass material is contacted with the solvent at a temperature in the range from ambient to just below the boiling point of the solvent.

In an alternate embodiment the biomass material is contacted with the solvent at a temperature above the boiling point of the solvent. In this embodiment this process step is carried out under pressure, for example in an autoclave.

In yet another embodiment the step of contacting the biomass is carried out under conditions of temperature and pressure at which the solvent is a super-critical fluid. Water is a super-critical fluid at temperatures above 374° C., corresponding to pressures above 22 MPa. Carbon dioxide is another example of a suitable solvent when in the form of a supercritical fluid. For $CO_2$ the critical point is at about 77° C. and about 7.4 MPa pressure.

Any solid/liquid separation technique can be used for separating the solvent from the partially demineralized biomass material. Examples include filtration, pressing, centrifugation, and the like.

For reasons of cost and safety, the solvent preferably is an aqueous liquid. The term aqueous liquid as used herein encompasses water, and aqueous solutions of materials that assist in dissolving minerals from biomass material. Examples of such assisting materials include acids and bases.

The demineralization step can comprise (a) swelling the biomass material in the solvent; and (b) removing at least part of the solvent by applying pressure to the swollen biomass material. Sub-step (b) can be carried out, for example, in a filter press or a kneader. It can be advantageous to repeat sub-steps (a) and (b) at once or several times. Repeating these steps results in removal of a greater portion of the minerals present in the biomass material; this gain is subject, however, to the law of diminishing returns.

An important aspect of the process of the present invention is that the solid, cellulose-containing biomass material is contacted with the Ionic Liquid medium under sub-solvating conditions. The term "sub-solvating conditions" as used herein refers to conditions such as the temperature of the Ionic Liquid medium, the water content of the Ionic Liquid medium, the presence or absence of a Brønstedt acid in the Ionic Liquid medium, and the contact time of the solid biomass material with the Ionic Liquid medium, selected to result in less than complete dissolution of the cellulose component of the biomass material in the Ionic Liquid medium.

In general, the aim of the pretreatment process of the present invention is to dissolve less than 10% of the dry weight of the solid biomass material in the Ionic Liquid medium, preferably less than 5% of the dry weight.

It is in general inevitable that some of the biomass material becomes dissolved in the Ionic Liquid during the pretreatment process. Dissolved biomass material, typically cellulose and/or hemicellulose, can be recovered from the Ionic Liquid medium by further reducing the cellulose dissolution properties of the Ionic Liquid medium. For example by lowering the temperature, and/or adding a non-solvent for cellulose, such as water. (Hemi)cellulose recovered from the Ionic Liquid medium can be mixed with the pretreated biomass material for joint processing.

In an alternate embodiment, dissolved biomass material is converted to a desired material, such as a liquid fuel, or a platform chemical, while it is dissolved in the Ionic Liquid medium. If the conversion product is insoluble in the Ionic Liquid medium, separation of the conversion product from the Ionic Liquid medium is facilitated.

As biomass material that becomes dissolved in the Ionic Liquid medium is not wasted, but can be recovered or used, it is possible to purposely operate the pretreatment process such that significantly more than 10% by weight of the solid biomass material becomes dissolved in the Ionic Liquid medium. It can be desirable to do so to obtain a desired degree of pretreatment of the biomass material, and/or to obtain a desired amount of dissolved cellulose for conversion to platform chemicals, for example.

One method of contacting the cellulose-containing biomass material with the Ionic Liquid medium under sub-solvating conditions comprises limiting the contact time of the solid biomass material with the Ionic Liquid medium to be below a predetermined maximum contact time. The maximum contact time can be readily determined in laboratory scale experiments.

Another method of contacting the cellulose-containing biomass material with the Ionic Liquid medium under sub-solvating conditions comprises controlling the contact temperature of the solid biomass material with the Ionic Liquid medium to be below a predetermined maximum contact temperature. The maximum contact temperature can be readily determined in laboratory scale experiments.

Another method of contacting the cellulose-containing biomass material with the Ionic Liquid medium under sub-solvating conditions comprises controlling the water content of the Ionic Liquid medium to be above a predetermined minimum water content. The minimum water content can be readily determined in laboratory scale experiments. It should be recognized that the biomass material itself introduces water into the system. This contribution must be taken into account if water content is used as a parameter to maintain sub-solvating conditions.

The Ionic Liquid medium can comprise an organic cation. In particular dicationic organic Ionic Liquids are excellent solvents for cellulose and hemicellulose. Several organic Ionic Liquids have been reported in the literature as being capable of (partially) dissolving the lignin component of lignocellulosic materials. Organic Ionic Liquids also have major disadvantages, the most important ones being high cost, and limited temperature resistance. Many have the additional disadvantage that they are poor solvents for cellulose when contaminated with water.

Preferred Ionic Liquids are inorganic Ionic Liquids, in particular inorganic molten salt hydrates. As compared to organic Ionic Liquids, inorganic Ionic Liquids are more temperature stable, and have a lower cost. In addition, in particular the inorganic molten salt hydrates are effective solvents for cellulose even in the presence of water. In fact, as their name indicates, a certain amount of water needs to be present for these materials to function as Ionic Liquid media.

Inorganic Ionic Liquids have an inorganic anion. The anion can contain a halogen atom. Examples include halides, oxyhalides and hydroxyhalides, in particular chloride, oxychlorides, and hydroxychlorides. The anion can also be hydroxide; for example, the hydroxide of the Cu/ammonia complex is a suitable Ionic Liquid medium for use in the process of the present invention.

The molten salt hydrate further comprises a cation, in particular Zn, Ba, Ca, Li, Al, Cr, Fe, or Cu.

Mixtures of inorganic salts can also be used, in particular eutectic mixtures. In general, any salt or salt hydrate that is liquid at a temperature of 200° C. or below, and is capable of dissolving cellulose, is suitable as the Ionic Liquid medium in the process of the present invention.

Particularly preferred are the hydrates of $ZnCl_2$, in particular $ZnCl_2.4H_2O$.

Preferably, the pretreatment process comprises the further strep (ii) of separating the pretreated solid biomass material from the Ionic Liquid medium. Any solid/liquid separation technique can be used for this purpose. Examples of suitable techniques include filtration, centrifugation, and decantation.

Preferably the process comprises the further step (iii) of removing at least part of the dissolved biomass material from the Ionic Liquid medium obtained in step (ii). This step can comprise precipitating the dissolved biomass material (primarily cellulose and/or hemicellulose) from the Ionic Liquid medium, for example by lowering the temperature and/or mixing the Ionic Liquid with a cellulose non-solvent, such as water or a lower alcohol.

In an alternate embodiment the dissolved cellulose is derivatized in situ, for example to cellulose acetate. The term "derivatization" as used herein refers to any chemical reaction that changes the chemical nature of cellulose, while leaving the cellulose backbone structure in tact. The cellulose derivative may be insoluble in the Ionic Liquid medium, in which case it spontaneously precipitates from the solution. If the cellulose derivative is soluble in the Ionic Liquid medium it can be removed therefrom by mixing the Ionic Liquid medium with a non-solvent for the derivative. In general, water and the lower alcohols are suitable non-solvents.

In yet another embodiment dissolved cellulose is chemically converted to a reaction product that is insoluble in the Ionic Liquid medium. For example, cellulose can be hydrolyzed in solution to glucose. In turn, glucose can be converted, using a sequence of hydrogenation and dehydration steps, to isosorbide, which is insoluble in most Ionic Liquid media.

In a preferred embodiment the process comprises the additional step (iv) of regenerating the Ionic Liquid medium obtained in step (iii). This additional regeneration step can comprise removing water from the Ionic Liquid medium. The regeneration step can comprise removing undissolved material from the Ionic Liquid medium.

The removal of water can generally be accomplished by distillation. For example, step (iv) may be carried out under increased pressure, at temperatures exceeding 100° C. By releasing the pressure while the temperature of the Ionic Liquid medium is maintained above 100° C., water is flashed off in a process sometimes referred to as flash-distillation.

After regeneration the Ionic Liquid medium may be recycled to step (i) of the process. This feature is particularly useful if the process is conducted in continuous mode. It will be understood, however, that the process can be conducted in batch mode as well.

The pretreated biomass material obtained by the pretreatment process of the present invention can be used in any process that benefits from the textural changes of the lignocellulosic composite caused by the pretreatment process.

In one embodiment the pretreated biomass material is used as a feedstock for enzymatic hydrolysis. In a preferred enzymatic hydrolysis process cellulose is converted to glucose. In a further preferred embodiment glucose is enzymatically converted to ethanol.

In a second embodiment the pretreated biomass material is used as a feedstock for thermal pyrolysis. The term "thermal pyrolysis" as used herein refers to conversion of the feedstock by exposing the feedstock to an elevated temperature, in the substantial absence of oxygen and a catalyst. Temperatures used in thermal pyrolysis generally range from about 350° C. to about 600° C. Higher temperatures may be used if the objective of the pyrolysis process is the production of gaseous conversion products, for example syngas.

The term "thermal pyrolysis" encompasses flash pyrolysis, which is characterized by high heating rates and short reaction times. A particulate heat transfer medium may be used to achieve the desired high heating rates. For the purpose of the present invention, a particulate heat transfer medium is considered not to be a catalyst, regardless of its composition, if its specific surface area, as determined by nitrogen adsorption using the Brunauer-Emmett-Teller (BET) method, is 1 $m^2/g$ or less.

In a third embodiment the pretreated biomass material is used as a feedstock for catalytic pyrolysis. Like thermal pyrolysis, catalytic pyrolysis comprises subjecting the feedstock to an elevated temperature in the substantial absence of oxygen. In catalytic pyrolysis the biomass material is contacted with a catalyst during the exposure to the elevated temperature. For the purpose of the present invention, a material is considered to be a catalyst, regardless of its composition, it its specific surface area, as determined by nitrogen adsorption using the Brunauer-Emmett-Teller (BET) method, is more than 1 $m^2/g$.

In a fourth embodiment the pretreated biomass material is used as a feedstock for hydrotreatment. The term "hydrotreatment" as used herein refers to any process in which the feedstock is contacted with hydrogen at an elevated temperature. Hydrotreatment can advantageously be carried out in the presence of a catalyst. Hydrotreatment catalysts known from the oil refinery art can be used for this purpose. In many cases hydrotreatment is carried out under elevated pressure, for example under hydrogen partial pressures in the range of from 5 bar to 200 bar.

Hydrocracking is a specific form of hydrotreatment. The term refers to a process wherein the feedstock is contacted with hydrogen in the presence of a catalyst having cracking properties. In general, a catalyst has cracking properties if it contains acidic sites. Zeolites are frequently used as cracking catalysts, in particular zeolite-Y and ZSM-5. In many cases the catalyst comprises a hydrogenating metal, in addition to the solid acid. Examples of hydrogenating metals include Ni, Fe, and the Pt-group metals.

The invention claimed is:

1. A process for pretreating a solid, cellulose-containing biomass material, said process comprising:
   (i) contacting the solid biomass material with an Ionic Liquid medium under sub-solvating conditions, wherein less than 10% of the dry weight of the solid biomass material is dissolved in the Ionic Liquid medium;
   (ii) separating pretreated solid biomass material from the Ionic Liquid medium; and
   (iii) subjecting the solid pretreated biomass to enzymatic hydrolysis, thermal pyrolysis, catalytic pyrolysis, hydrotreatment or hydrocracking.

2. The process of claim 1 wherein less than 5% of the dry weight of the solid biomass material is dissolved in the Ionic Liquid medium.

3. The process of claim 1 wherein sub-solvating conditions are obtained by controlling the contact time of the solid biomass material with the Ionic Liquid medium to be below a selected maximum contact time whereby less than 10% of the dry weight of the solid biomass material is dissolved in the Ionic Liquid medium.

4. The process of claim 1 wherein sub-solvating conditions are obtained by controlling the contact temperature of the solid biomass material with the Ionic Liquid medium to be below a selected maximum contact temperature whereby less than 10% of the dry weight of the solid biomass material is dissolved in the Ionic Liquid medium.

5. The process of claim 1 wherein sub-solvating conditions are obtained by controlling the water content of the Ionic Liquid medium to be above a selected minimum water content whereby less than 10% of the dry weight of the solid biomass material is dissolved in the Ionic Liquid medium.

6. The process of claim 1 wherein the Ionic Liquid comprises an organic cation or a molten salt hydrate.

7. The process of claim 6 wherein the molten sat hydrate comprises a halogen anion.

8. The process of claim 7 wherein the halogen anion is chloride.

9. The process of claim 6 wherein the molten salt hydrate comprises a cation selected from the group consisting of Zn, Ba, Ca, Li, Al, Cu, Fe, $Cu(NH_3)_x$ and Cr.

10. The process of claim 6 wherein the Ionic Liquid is a molten salt hydrate comprising $ZnCl_2$, $CaCl_2$, LiCl, or a mixture thereof.

11. The process of claim 1 comprising the further step of removing dissolved biomass material from the Ionic Liquid medium obtained in step (ii).

12. The process of claim 11 comprising the further step of regenerating the Ionic Liquid medium.

13. The process of claim 12 wherein the step of regenerating comprises removing undissolved material from the Ionic Liquid medium.

14. The process of claim 12 wherein the step of regenerating comprises adjusting the water content of the Ionic Liquid medium.

15. The process of claim 12 comprising the further step of recycling the Ionic Liquid medium to step (i).

16. The process of claim 15 wherein the process is a continuous process.

17. The process of claim 11 comprising recovering the dissolved biomass material.

18. The process of claim 17 further comprising mixing the recovered biomass material with the pretreated biomass material for joint processing.

19. The process of claim 1 wherein the enzymatic hydrolysis produces glucose.

* * * * *